United States Patent
Bindlish

(10) Patent No.: US 11,249,446 B2
(45) Date of Patent: Feb. 15, 2022

(54) NONLINEAR MODEL PREDICTIVE CONTROL OF A PROCESS

(71) Applicant: Dow Global Technologies LLC, Midland, MI (US)

(72) Inventor: Rahul Bindlish, Houston, TX (US)

(73) Assignee: Dow Global Technologies LLC, Midland, MI (US)

(*) Notice: Subject to any disclaimer, the term of this patent is extended or adjusted under 35 U.S.C. 154(b) by 115 days.

(21) Appl. No.: 16/663,737

(22) Filed: Oct. 25, 2019

(65) Prior Publication Data

US 2021/0124316 A1 Apr. 29, 2021

(51) Int. Cl.
| | | |
|---|---|---|
| G05B 13/04 | (2006.01) | |
| C07C 29/152 | (2006.01) | |
| G05B 13/02 | (2006.01) | |
| G05B 19/05 | (2006.01) | |
| G06F 17/18 | (2006.01) | |

(52) U.S. Cl.
CPC .......... *G05B 13/048* (2013.01); *C07C 29/152* (2013.01); *G05B 13/0285* (2013.01); *G05B 19/058* (2013.01); *G06F 17/18* (2013.01); G05B 2219/24075 (2013.01)

(58) Field of Classification Search
CPC ........... G05B 13/048; G05B 19/058; G05B 13/0285; G05B 2219/24075; C07C 29/152; G06F 17/18
USPC ....................................................... 700/28
See application file for complete search history.

(56) References Cited

U.S. PATENT DOCUMENTS

| | | | |
|---|---|---|---|
| 4,349,869 A | | 9/1982 | Prett et al. |
| 5,740,033 A | * | 4/1998 | Wassick ............... G05B 13/048 700/29 |
| 6,056,781 A | | 5/2000 | Wassick et al. |
| 7,203,555 B2 | * | 4/2007 | Ogunnaike ............. G05B 5/01 700/28 |
| 2,414,149 A1 | | 8/2008 | Decourcy et al. |
| 8,389,751 B2 | | 3/2013 | Zhang et al. |
| 8,504,175 B2 | | 8/2013 | Pekar et al. |
| 9,649,621 B2 | | 5/2017 | Shibata et al. |
| 9,908,861 B2 | | 3/2018 | Shibata et al. |
| 2008/0255814 A1 | * | 10/2008 | Chia .................... G05B 13/048 703/6 |

(Continued)

OTHER PUBLICATIONS

A. Singh et al., Journal of Process Control 23 (2013) 294-305.

(Continued)

*Primary Examiner* — Jigneshkumar C Patel
(74) *Attorney, Agent, or Firm* — Quarles & Brady LLP

(57) ABSTRACT

A chemical system for an operation exhibiting steady-state gain inversion is provided herein and includes a reactor configured to receive a feed stream and produce an outlet stream to form a process and a control device configured to control a process. The control device receives inputs indicative of an operational parameter and output variables and, in response to the inputs and output variables, provides a steady-state manipulated input configured to control or optimize the process. The control device includes an input disturbance model, a state estimator, a non-linear steady-state target calculator, and a regulator configured to provide a signal for adjustment of one or more inputs based on the steady-state manipulated input and associated output variables.

14 Claims, 12 Drawing Sheets

(56) References Cited

U.S. PATENT DOCUMENTS

2010/0268353 A1    10/2010  Crisalle et al.
2014/0316150 A1 *  10/2014  Zhang ................. C07D 301/10
                                                      549/534

OTHER PUBLICATIONS

S. Patwardhan et al., Computers chem. Engng vol. 22, No. 4/5, pp. 587-601, 1998.
P. Daoutidis et al., Chemical Engineering Science, vol. 47, No. 4, pp. 837-849, 1992.
P. Sistu et al., Chemical Engineering Science, vol. 50, No. 6, pp. 921-936, 1995.

* cited by examiner

NONLINEAR MODEL PREDICTIVE CONTROL OF A PROCESS

BACKGROUND

The production of alkylene oxide can be accomplished via a chemical system that utilizes catalytic epoxidation of olefins in the presence of oxygen using silver based catalysts. Conventional silver-based catalysts used in such processes typically provide a relatively lower efficiency or "selectivity" (e.g., a lower percentage of the reacted alkylene is converted to the desired alkylene oxide). In some processes, when using conventional catalysts in the epoxidation of ethylene, the theoretically maximal efficiency towards ethylene oxide, expressed as a fraction of the ethylene converted, does not reach values above the 6/7 or 85.7 percent limit.

Certain such catalysts, such as so-called "high selectivity" or "high efficiency" catalysts, tend to exhibit relatively steep efficiency curves as a function of gas phase promoter concentration as the concentration moves away from the value that provides a high efficiency (e.g., the change in efficiency with respect to a change in gas phase promoter concentration is at least 0.2%/ppmv when operating away from the efficiency maximizing promoter concentration). Thus, small changes in the promoter concentration can result in significant efficiency changes as the efficiency can exhibit a pronounced maximum, e.g., an optimum, at certain concentrations (or feed rates) of the gas phase promoter over time. The pronounced maximum of the chemical process is due to multi-phase flows and chemical reactions which are characterized by process nonlinearities and time delays due to mass transport and chemical reaction rates.

As many of the variables in the chemical process have nonlinear relationships with other variables, e.g., inter-loop interaction of variables, process models need to be developed to effectively characterize these multi-interdependent variable relationships, which may also be non-linear. In various implementations, a Linear Model Predictive Control (LMPC), among other approaches, has been proposed for applications in the field of process control. However, such approaches have continued to lack stability with processes having a steady-state gain inversion.

SUMMARY

In some embodiments, a chemical system for an operation exhibiting steady-state gain inversion includes a reactor configured to receive a feed stream and produce an outlet stream to form a process and a control device configured to control a process. The control device receives inputs indicative of an operational parameter and output variables and, in response to the inputs and output variables, provides a steady-state manipulated input configured to control or optimize the process. The control device includes an input disturbance model based on using the steady-state manipulated input as a custom output measurement to determine unmeasured disturbances, a state estimator configured to utilize the custom output measurement to estimate the unmeasured disturbances entering the process and thereby predict a change in the process based on a characterization of the process by the model, a non-linear steady-state target calculator configured to determine the steady-state manipulated input for the process based on the characterization of the process as calculated by the model, and a regulator configured to provide a signal for adjustment of one or more inputs based on the steady-state manipulated input and associated output variables.

In some embodiments, a method for controlling a chemical system through a control device includes receiving inputs indicative of an operational parameter of a process and a steady-state output variable. The method also includes implementing an input disturbance model based on using an optimum manipulated steady-state input as a custom output measurement to determine the optimized manipulated input in a presence of both measured and unmeasured disturbances. In addition, the method includes estimating a state of the process to predict the process based on a characterization of the process by the model. The method further includes determining an a targeted manipulated input for the process based on the characterization of the process by the modelling and the estimating of the one or more steady-state output variables of the chemical system. Lastly, the method includes regulating the process based on the targeted manipulated input.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DEFINITIONS

Figure 1:
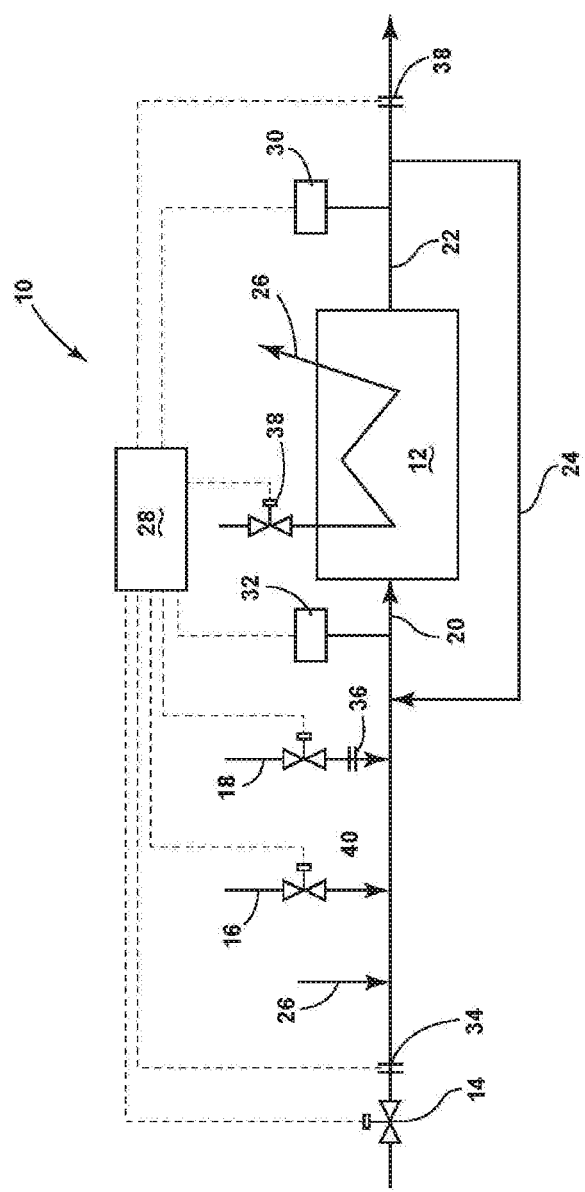
FIG. 1 is a process flow diagram depicting an embodiment of a process for making an alkylene oxide by epoxidizing an olefin, in accordance with an embodiment of the present disclosure.

All references to the Periodic Table of the Elements herein shall refer to the Periodic Table of the Elements, published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percentages are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower value and the upper value. For ranges containing explicit values (e.g., a range from 1, or 2, or 3 to 5, or 6, or 7) any subrange between any two explicit values is included (e.g., the range 1-7 above includes subranges 1 to 2; 2 to 6; 5 to 7; 3 to 7; 5 to 6; etc.).

Unless stated to the contrary, implicit from the context, or customary in the art, all parts and percentages are based on weight, and all test methods are current as of the filing date of this disclosure.

The term "composition," as used herein, refers to a mixture of materials which comprise the composition, as well as reaction products and decomposition products formed from the materials of the composition.

The term "alkylene oxide," as used herein, has the structure A below:

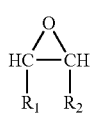

Structure A wherein, R1 and R2 are individually selected from the group consisting of hydrogen and alkyl radicals having from 1 to 6 carbon atoms. For example, the alkylene oxide can be a propylene oxide (R1=CH3, R2=H) or an ethylene oxide (R1=R2=H).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The terms "operably connected" or "operably coupled" includes any two components that in combination achieve a desired functionality. Some examples of operably coupled include, but are not limited to, physically makeable components, physically interacting components, wirelessly interacting components, wirelessly interacting components, logically interacting components, and/or logically interacting components.

A "control device" includes any combination of software and/or processing circuitry suitable for controlling various components described herein including, without limitation, processors, microcontrollers, application-specific integrated circuits, programmable gate arrays, and any other digital and/or analog components, as well as combinations of the foregoing, along with inputs and outputs for transceiving control signals, drive signals, power signals, sensor signals, and so forth. All such computing devices and environments are intended to fall within the meaning of the terms "control device," "controller," or "processor" as used herein unless a different meaning is explicitly provided or otherwise clear from the context.

An "ethylene oxide" is a cyclic ether (epoxide) having the formula $C_2H_4O$ and Structure B below.

Structure B

DETAILED DESCRIPTION

The present disclosure provides a chemical system implementing a nonlinear model predictive control (NMPC) device augmented with an appropriate disturbance model that is capable of generally solving the nonlinear constrained optimization problem without formulating an unconstrained control law. The control device provided herein may ensure sufficient robustness for controlling the process at the optimal point (e.g., a "peak"), or within a desired or optimal range, where a steady-state gain process changes sign. In addition, the control device provided herein manipulates inputs to generally maintain a process near the peak where steady-state gain inversion happens in presence of disturbances instead of operating away from that point to prevent instability.

Controlling a process with steady-state gain inversion at the optimal point in the presence of measured disturbances can lead to frequent sign changes in steady-state gain and needs an appropriate estimation of disturbances for proper control action that maximizes the controlled output. Problems can arise in applications that control actual industrial processes with gain inversion due to significant process disturbances and potential modeling errors thereby increasing the importance of a robust solution. Thus, the chemical system provided herein can be configured to maximize an output variable that has steady-state gain inversion with respect to the manipulated input through the use of the observed optimized manipulated steady-state input as a custom output measurement that is available infrequently. The chemical system also implements an input disturbance model that utilizes the infrequent custom output measurement to maximize the output variable with steady-state gain inversion.

Referring now to FIG. 1, a chemical system 10 capable of making an alkylene oxide includes a reactor 12 in accordance with an embodiment of the present disclosure. An olefin feed stream 14, which includes saturated hydrocarbons, such as ethane, as an impurity, is combined with an oxygen feed 16 and a gas phase promoter feed 18 to define a reactor feed stream 20 proximate to a reactor inlet. A reactor product stream 22 includes the alkylene oxide product, plus side products (e.g., $CO_2$, $H_2O$, and small amounts of saturated hydrocarbons), unreacted olefin, oxygen, and inerts. In some commercial processes, the alkylene oxide product along with some water product can be removed from the reactor product stream 22 in an alkylene oxide recovery unit. If desired, a recycle stream 24 may also be provided to recycle the unreacted olefins and oxygen. However, if a recycle stream 24 is implemented, a purge line can be provided to reduce the buildup of impurities and/or side products, such as argon and ethane. In addition, in some embodiments, the plant 10 also includes a carbon dioxide removal step that is performed upstream of where the recycle stream 24 combines with the fresh feed stream 20 prior to entering the reactor 12.

In an embodiment, the olefin provided by the feed stream 14 is ethylene. Additionally or alternatively, in an embodiment, the olefin feed stream 14 may include aromatic olefins, di-olefins, whether conjugated or not, C2-C12 α-olefins, and/or C2-C8 α-olefins. The oxygen feed 16 may include substantially pure oxygen or air. If pure oxygen is used, ballast gases or diluents 26, such as nitrogen or methane, may also be included to maintain the oxygen concentration below the maximum level allowed by flammability considerations. The concentration of oxygen in the reactor feed stream 20 varies over a wide range, and in practice, flammability can be the limiting factor for oxygen concentration.

When present, the carbon dioxide concentration in reactor feed stream 20 can have an adverse effect on the efficiency, activity, and/or stability of catalysts used in reactor 12. Carbon dioxide is produced as a reaction by-product and is introduced with other inlet reaction gases as an impurity. In various commercial ethylene epoxidation processes, at least part of the carbon dioxide is removed continuously in order to control its concentration to an acceptable level in the cycle.

The gas phase promoter is a compound that enhances the efficiency and/or activity of the chemical system 10 for producing the desired alkylene oxide. In an embodiment, the gas phase promoters include organic chlorides. For example, the gas phase promoter is at least one selected from the group consisting of methyl chloride, ethyl chloride, ethylene dichloride, vinyl chloride, and mixtures thereof. In various embodiments, ethyl chloride and ethylene dichloride can be the gas phase promoter feed stream 18. Using chlorohydrocarbon gas phase promoters as an example, it is believed that the ability of the promoter to enhance the performance (e.g., efficiency and/or activity) of the chemical system 10 for the desired alkylene oxide depends on the extent to which the gas phase promoter chlorinates the surface of the catalyst in reactor 12, for example, by depositing particular chlorine species such as atomic chlorine or chloride ions on the catalyst. However, hydrocarbons lacking chlorine atoms are believed to strip chlorides from the catalyst, and therefore, detract from the overall performance enhancement provided by the gas phase promoter. Paraffinic compounds, such as ethane or propane, are believed to be especially effective at stripping chlorides from the catalyst. However, olefins, such as ethylene and propylene, are also believed to act to strip chlorides from the catalyst. Some of these hydrocarbons may also be introduced as impurities in the ethylene feed stream 12 or may be present for other reasons (such as the use of recycle stream 24). In some embodiments, the concentration of ethane in the reactor feed stream 20, when present, is from 0 to about 2 mole percent. Given the competing effects of the gas phase promoter and the chloride-removing hydrocarbons in reactor feed stream 20, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity Z and represented by the following formula:

$$Z = \frac{\text{ethyl chloride equivalent } (ppmv)}{\text{ethane equivalent (mole percent)}}, \quad (1)$$

wherein the ethyl chloride equivalent is the concentration in ppmv (which is equivalent to ppm mole) of ethyl chloride that provides substantially the same catalyst chloriding effectiveness of the organic chlorides present in reactor feed stream 20 at the concentrations of the organic chlorides in feed stream 20; and the ethane equivalent is the concentration of ethane in mole percent that provides substantially the same catalyst dechloriding effectiveness of the non-chloride containing hydrocarbons in the reactor feed stream 20 at the concentrations of the non-chloride containing hydrocarbons in the reactor feed stream 20.

Although the gaseous chlorine-containing promoter may be supplied as a single species, upon contact with the catalyst, other species may be formed leading to a mixture in the gas phase. Consequently, if the reaction gases are recycled such as via the recycle stream 24, a mixture of species will be found in the inlet of the reactor 12. In particular, the recycled reaction gases at the inlet may contain ethyl chloride, vinyl chloride, ethylene dichloride and or methyl chloride, even though only ethyl chloride or ethylene dichloride is supplied to the fresh feed stream 20.

The order in which the inlet gases (alkylene, oxygen, and ballast gas) and gas phase promoter are mixed may be varied, and mixing may occur simultaneously or sequentially. The order of mixing of the gaseous components of the process is chosen for convenience reasons, for safety reasons, and/or for any other reason. For example, oxygen is added after the ballast gas for reasons of safety. However, in some embodiments, the gas phase promoter should be present in the reactor feed stream 20 as it is introduced to the solid catalyst in reactor 12.

Non-limiting examples of suitable reactors for reactor 12 include a fixed bed tubular reactor, a continuous stirred tank reactor (CSTR), and a fluid bed reactor. The particular mode of operation selected can be dictated by process economics. The epoxidation reaction is exothermic. Thus, a coolant system 26 (e.g., a cooling jacket or a hydraulic circuit with a coolant fluid such as a heat transfer fluid or boiling water) is provided to regulate the temperature of reactor 12. The reaction temperature is selected to provide the desired yield of ethylene oxide. In an embodiment, the epoxidation reaction is carried out at a temperature that is at least 200° C., or at least 210° C., or at least 220° C. In various embodiments, reaction temperatures of no more than 300° C. or reaction temperatures of no more than 290° C. are implemented. The reactor pressure is selected based on the desired mass velocity and productivity and ranges from 5 atm (506 kPa) to 30 atm (3.0 MPa). The gas hourly space velocity (GHSV) is greater than 3000 $hr^{-1}$, greater than 4,000 $hr^{-1}$, or greater than 5,000 $hr^{-1}$.

Catalysts for the production of alkylene oxide, for example, ethylene oxide or propylene oxide, may be prepared by impregnating a suitable carrier material with a solution of one or more silver compounds, followed by treatment to reduce and deposit silver throughout the pores of the carrier. Generally, the carrier is impregnated with a catalytic amount of silver, which is any amount of silver capable of catalyzing the oxidation of the alkylene with oxygen or an oxygen-containing gas to the corresponding alkylene oxide.

In an embodiment, a variety of promoters, that is, materials which, when present in combination with particular catalytic materials, for example, silver, benefit one or more aspect of catalyst performance or otherwise act to promote the catalyst's ability to make a desired product, for example ethylene oxide or propylene oxide. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor 12, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst varies over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, operability (resistance to run-away), efficiency, activity, conversion, stability, and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

The performance of the epoxidation process is assessed based on the selectivity, the catalyst's activity, and/or the stability of operation during a process. The selectivity is the molar fraction of the converted olefin yielding the desired olefin oxide. In some cases, in ethylene oxide production, the operator of chemical system 10 would think that, in the absence of constraints, in order to maximize selectivity, they would have to utilize higher ethylene, higher oxygen, and lower $CO_2$ levels. However, due to the steady-state gain inversion characteristics of some processes, if a catalyst is operating at high temperatures and the temperature is reduced, a selectivity gain will be observed. But as the temperature is reduced further, the degree of selectivity gain becomes smaller, and then finally a selectivity maximum is reached. As the temperature is further decreased, selectivity also decreases.

In an embodiment, the chemical system 10 described herein can be used in open-loop or closed-loop processes that maintain a process at or near optimal point during operation of the plant 10. In both processes, a control device 28 is utilized for regulating one or more inputs. For example, a control device 28 is provided which receives inputs from an effluent concentration analyzer 30 operably coupled with the reactor outlet stream 22, a reactor feed concentration analyzer 32 operably coupled with the feed stream 20, an olefin feed flow meter 34 downstream of the olefin feed stream 14, a gas phase promoter feed flow meter 36 downstream of the gas phase promoter feed stream 18, and a flow meter 38 operably coupled with the coolant system 26. The control device 28 is implemented in a computerized control system and also includes a central processing unit and a memory as well as outputs that are ultimately used to adjust control valves for regulating the inputs. Based on the received inputs, the control device 28 determines the mole percentage of alkylene oxide in the reactor effluent in the reactor stream 22 and a gas-phase promoter effectiveness parameter (e.g., Z) for reactor feed stream 20.

For ethylene oxide production, the gas-phase promoter is one or more chlorinated hydrocarbons. Accordingly, the control device 28 also receives concentration data for chlorinated hydrocarbons such as ethyl chloride, vinyl chloride, and ethylene dichloride, as well as the concentration of ethylene, ethane, and other non-chlorinated hydrocarbons in the reactor feed stream 20 from the analyzer 32. The concentration data is then used to calculate the overall chloriding effectiveness (e.g., Z). The control device 28 also receives a user-entered setpoint for the mole percent of alkylene oxide in reactor effluent in the reactor outlet stream 22 and/or the yield of alkylene oxide. Based on the user-entered setpoint and data from the analyzer 30, the control device 28 determines if the concentration of alkylene oxide in reactor outlet stream 22 and/or the yield of alkylene oxide is within a predetermined range of the user-entered setpoint. When the alkylene oxide concentration and/or yield falls outside of the predetermined range, the control device 28 either adjusts the reaction temperature or the flow rate of the gas phase promoter (to change the value of the gas-phase promoter effectiveness parameter), and/or any other variable input.

The control device 28 is provided to regulate the olefin concentration in the reactor feed stream 20. In the illustrated embodiment, the control device 28 receives compositional data from the analyzer 32 indicating the amount of olefin in the reactor feed stream 20. The control device 28, which has a user-entered setpoint for the olefin concentration in reactor feed stream 20, receives flow data from flow meter 34 and manipulates a control valve fluidly coupled with the olefin feed stream 12 to control the flow thereof. The control device 28 may be analog or digital and is implemented in a computerized distributed control system. The illustrated control scheme is merely exemplary and is not meant to limit the scope of the present disclosure.

Figure 2:
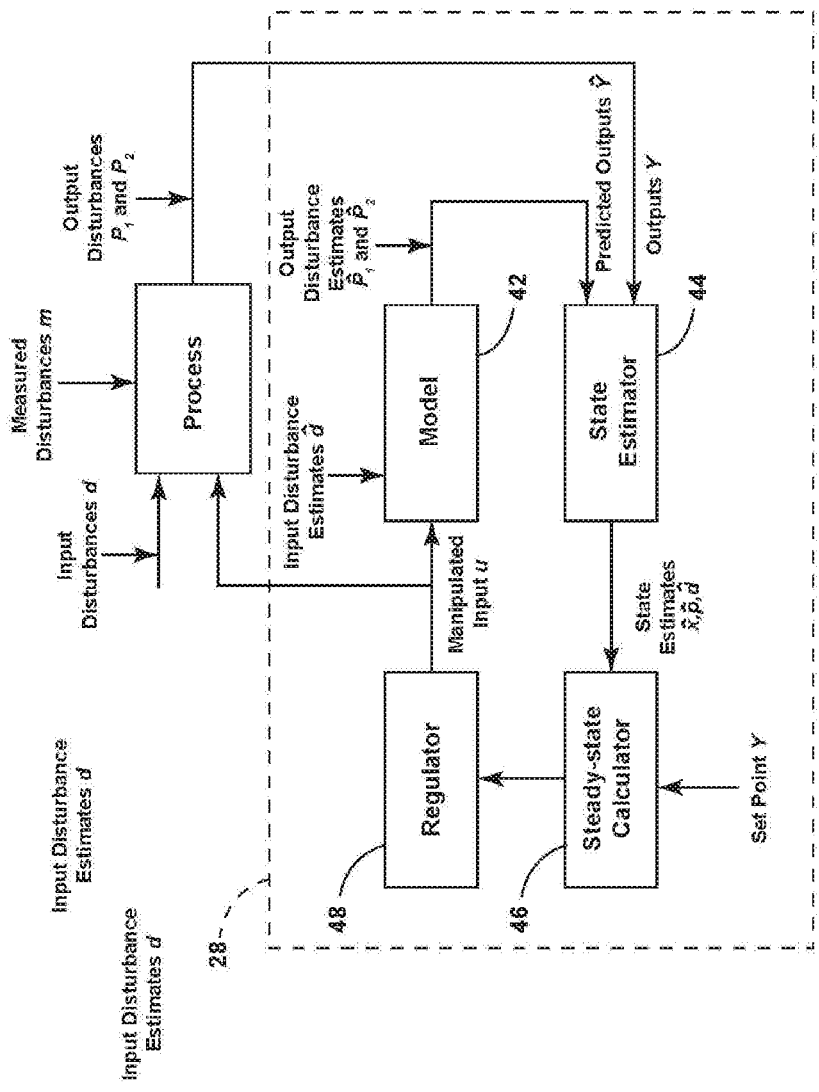
FIG. 2 is a schematic diagram of a nonlinear model predictive control (NMPC) device for a process with steady-state gain inversion, in accordance with an embodiment of the present disclosure.

With reference to FIG. 2, in order to achieve the goals of stability and maximum profitability for the chemical system, the control device 28 has various modules that include a model 42 of the chemical system 10, a state estimator 44 configured to simulate the operation of the chemical system 10 to predict the operation of the chemical system 10, a steady-state calculator 46 operative to determine an optimized manipulated input for operating the chemical system 10, and/or a regulator 48 configured to adjust the chemical system 10 based on the optimized manipulated input. The "model," the "state estimator," the "calculator," and/or the "regulator" described in this specification have been labeled as modules in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices, such as field programmable gate arrays, programmable array logic, programmable logic devices, or the like.

Modules may also be implemented in software for execution by various types of processors. An identified module of executable code may, for example, comprise one or more physical or logical blocks of computer instructions which may, for example, be organized as an object, procedure, or function. Nevertheless, the executables of an identified module need not be physically located together, but may comprise disparate instructions stored in different locations which, when joined logically together, comprise the module and achieve the stated purpose for the module.

A module of executable code may be a single instruction, or many instructions, and may even be distributed over several different code segments, among different programs, and across several memory devices. Similarly, operational data may be identified and illustrated herein within modules, and may be embodied in a suitable form and organized within a suitable type of data structure. The operational data may be collected as a single data set, or may be distributed over different locations including over different storage devices, and may exist, at least partially, merely as electronic signals on a system or network.

In an embodiment, the control device 28 of the chemical system 10 is configured to control an operation of the chemical system, wherein the control device receives inputs indicative of an operational parameter of the chemical system and the output variables and, in response to the inputs and output variables, provides a manipulated input to the chemical system for controlling and optimizing the operation of the chemical system. In various embodiments, this the control device 28 is configured as an NMPC device 28 and values are provided for manipulated inputs u (or input variables) to a plant 10 capable of implementing a controllable chemical process. In an embodiment, external unmeasured input disturbances d and/or measured disturbances m are provided to the plant. In response to receiving manipulated inputs u, input disturbances d and/or measured disturbances m, the plant 10 produces an output Y, which includes various output disturbances $P_1$, $P_2$. The output Y is fed to a state estimator 44.

A model 42 can be defined by non-linear and/or linear equations between at least one input and at least one output and operates in parallel with the plant 10. The nonlinear model 42 is a mathematical model of various processes of the plant 10 that provide predictive outputs $\hat{Y}$ similar to the plant 10 when each is supplied with the same inputs u. In various embodiments, the model 42 includes at least one of a steady state model, a dynamic model, an adaptive model, a fuzzy model and/or a neural network model.

In an embodiment, the model 42 characterizes the dynamic and steady-state response of the outputs in the chemical system 10 to the inputs received by it. In various embodiments, the non-linear model 42 receives the manipulated inputs u and estimated input disturbances $\hat{d}$. In response, the model 42 generates predicted outputs $\hat{Y}$ while factoring output disturbance estimates $\hat{P}_1$, $\hat{P}_2$. Thus, the model 42 of the chemical system 10 can be designed to accurately depict the functioning of the chemical system 10 and its control structures. To this end, the model 42 solves non-linear problems, and therefore can be computationally demanding due to a large number of computations required for each output calculation. But, to be practical, the model 42 should arrive at estimated outputs quickly while considering the costs of running a chemical system 10. Therefore, one of the control goals can include optimization (i.e. minimization) of operating costs instead of simply optimizing operation.

Figure 3:
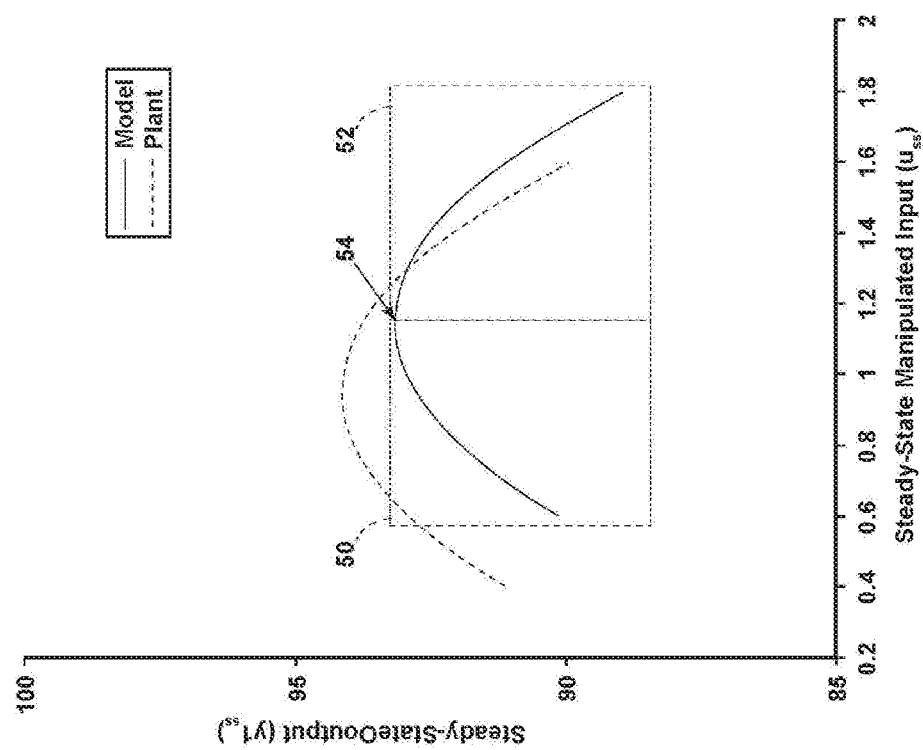
FIG. 3 is a graph depicting steady-state variations of an output based on a manipulated input, in accordance with an embodiment of the present disclosure.

In an embodiment, an input disturbance model based on using a steady-state manipulated input, which may be an optimum steady-state manipulated output, as a custom output measurement that is available infrequently to determine the location of the optimized manipulated input in a presence of both measured and unmeasured disturbances is used along with first order dynamics for maximizing the output variable $y_1$ that exhibits steady-state gain inversion with respect to the manipulated input u. The steady-state nonlinear model equations can be expressed as:

$$y_{1_{ss}} = l(u_{ss}, m) \tag{2},$$

$$y_{2_{ss}} = b^* u_{ss} \tag{3},$$

where $u_{ss}$ is the steady-state manipulated input, m is the measured disturbances, and $[y_{1_{ss}}, y_{2_{ss}}]$ are the steady-state controlled outputs. The output variable with steady-state gain inversion is denoted as $y_1$ along with various operational limits $y_2$ that infrequently become active constraints. The steady-state nonlinear model 42 has a quadratic variation for output $y_{1_{ss}}$ with respect to manipulated input u with a change in sign for the steady-state gain of $y_{1_{ss}}$ with respect to $u_{ss}$ at the peak where $y_{1_{ss}}$ is maximized, as illustrated in FIG. 3. In other embodiments, any other mathematical function may be utilized for determining a defined target range of a chemical process or operation. First order dynamics with varying steady-state gains and time constants can be used to define the effect of inputs u and m on outputs $y_1$ and $y_2$. Thus, in an embodiment, the steady-state nonlinear model 42 (equations (2) and (3)) along with first order dynamics can constitute the process model 42.

In an embodiment incorporating a NMPC, there are no guarantees for optimal control so disturbance models can be representative of the process disturbances along with plant-model mismatch and also take into account the control objectives. For a process that has steady-state gain inversion with a control objective of maximizing the output variable $y_1$ at the peak, or within a desired range of the peak, it can be important to locate the corresponding value of manipulated input robustly in the presence of disturbances and potential modeling errors. In an embodiment, the control device 28 is configured to estimate the unmeasured disturbances that shift a position of the optimum peak where steady-state gain inversion occurs. In various embodiments, the unmeasured disturbances can include catalytic aging or associated over/under performance of the reactor. An output disturbance model for the output variable $y_1$ is not likely to give the location of the optimum steady-state manipulated input u that is dependent on input or state disturbances. An input disturbance model for the manipulated input u that uses the error in the output variable $y_1$ may also need to know whether the process is on the positive gain or negative gain part of the steady-state variation curve, which is represented by region 50 and region 52, respectively, in FIG. 3 and separated by peak 54. Identification of the positive gain or negative gain is problematic close to the peak 54 for maximizing the output variable $y_1$ with noisy data, which is common for various industrial processes. The location of optimum steady-state manipulated input $u_{ss}^{opt}$ where the controlled output is maximized $y_{1_{ss}}^{opt}$ depends on measured disturbances m and unmeasured disturbances such that $$u_{ss}^{opt} = h(m), \quad (4)$$

$$\frac{\partial y_{1_{ss}}}{\partial u_{ss}} = 0, \text{ at } u_{ss} = u_{ss}^{opt}. \quad (5)$$

The optimum steady-state manipulated input $u_{ss}^{opt}$ is introduced as a custom output measurement $y_3$ that is available infrequently in the steady-state process model 42 (equations (2) and (3)). The augmented steady-state nonlinear model 42 equations can be expressed as:

$$y_{1_{ss}} = l(u_{ss}, m) \quad (6),$$

$$y_{2_{ss}} = b * u_{ss} \quad (7),$$

$$y_3 = u_{ss}^{opt} = h(m) \quad (8).$$

Figure 4:
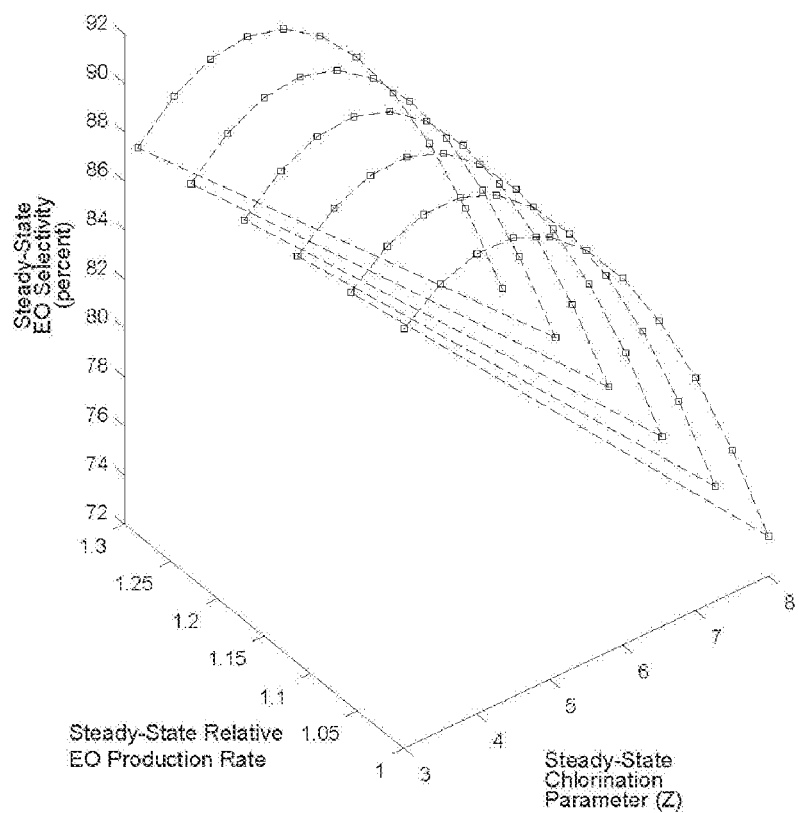
FIG. 4 is a graph depicting steady-state ethylene oxide (EO) selectivity, in accordance with an embodiment of the present disclosure.

At steady conditions, the expected optimum for $y_{1_{ss}}$ can occur after the control device 28 settling time $t_s$ and a new value for the optimum steady-state manipulated input $u_{ss}^{opt}$ or the output measurement $y_3$ can be observed. The model 42 for the operational limit $y_2$ that becomes active infrequently is linear and independent of the value of the optimum steady-state manipulated input $u_{ss}^{opt}$. Movement of u towards the optimum steady-state manipulated input $u_{ss}^{opt}$ at steady conditions for m, as generally illustrated in FIG. 4, over the settling time $t_s$ of the control device 28 can result in an increase in the output variable $y_1$ unless the location of the optimum steady-state manipulated input $u_{ss}^{opt}$ has changed and needs to be corrected by an input disturbance model 42. An input disturbance model is used to account for the actual location of the optimum steady-state manipulated input $u_{ss}^{opt}$ when a new peak 54 for the expected optimum is observed, as generally illustrated in FIG. 3, at steady conditions for the measured disturbances m. Various algorithms or models can be used to update the mismatch in location of the optimum steady-state manipulated input $u_{ss}^{opt}$ or the steady state output measurement $y_3$ based on the observation of a new peak 54 for $y_{1_s}$ after all the following criteria are met for data over the settling time $t_s$ of the control device 28:

1. Manipulated input u is available to maximize the primary output $y_1$ instead of being constrained by operational limit $y_2$;
2. Measured disturbances m are steady as per defined statistical criteria;
3. Manipulated input u is steady or moving towards the optimum steady-state manipulated input $u_{ss}^{opt}$; and
4. A new optimum location is observed for the optimum steady-state manipulated input $u_{ss}^{opt}$ because the output variable $y_1$ decreases after the settling time $t_s$ of the control device.

Steady-state statistical criteria are defined for measured disturbances m by reviewing their standard deviation over the settling time of the control device 28 against appropriate limits. For example, the standard deviation is calculated as follows:

$$\sigma_m = \delta \quad (9).$$

In an embodiment, data filtering and screening is implemented for noisy output measurements y. For example, a digital filter is implemented with the control device 28 to filter the noise and include both an amplitude filter to clip signal spikes and glitches and/or a low pass filter to remove higher-order, noise-related frequencies from the signal that could adversely affect computational speed of the control device 28.

In embodiments in which a state space model 42 is implemented, a discretized state space model 42 for the steady-state nonlinear model 42 (equations (6), (7) and (8)) with first order dynamics at control device frequency k can be expressed as:

$$x_{1_{k+1}} = f(x_{1_k}, x_{3_k}, u_k, m_k) \quad (10),$$

$$x_{2_{k+1}} = x_{2_k} + a * u_k \quad (11),$$

$$x_{3_{k+1}} = x_{3_k} + h(m_k) \quad (12),$$

$$y_{1_{k+1}} = x_{1_{k+1}} \quad (13),$$

$$y_{2_{k+1}} = x_{2_{k+1}} \quad (14),$$

$$y_{3_{k+1}} = x_{3_{k+1}} \quad (15),$$

where $y_1$ is the maximized output variable with steady-state gain inversion, $y_2$ is controlled within safe operating limits, and $y_3$ denotes the location of the optimum steady-state manipulated input $u_{ss}^{opt}$ to maximize the output variable $y_1$. For some plant operations, the manipulated input u can be available to maximize the output variable $y_1$ through variable functions, some of which were described in reference to FIG. 1. Thus, the augmented state-space model can be written as:

$$X_{k+1} = F(X_k, u_k, m_k) \quad (16),$$

$$Y_{k+1} = X_{k+1} \quad (17),$$

where $X=[x_1, x_2, x_3]$ denotes the states of the model 42 and $Y=[y_1, y_2, y_3]$ denotes the output measurements.

With further reference to FIG. 3, in an embodiment, the control device 28, along with instructions stored within the memory of the control device 28, can be utilized for optimizing the output variable $y_1$ at the peak 54 where steady-state gain inversion occurs with respect to the manipulated input u.

In some embodiments, plant-model mismatch can be attributed to disturbances in output measurements instead of inputs or the process in the NMPC of the control device 28. Instructions stored in the memory of the control device 28 are used to implement an input disturbance model based on the custom output measurement, such as those defined herein to account for mismatch in the location of the optimum manipulated input u in presence of both measured and unmeasured disturbances. In order for the control device 28 to utilize the output measurement in an augmented state-space formulation (equations (16) and (17)), the control device 28 includes a state estimator 44 configured to simulate the operation of the chemical system 10 to predict the operation of the chemical system 10 based on the characterization of the chemical system 10 by the model 42. For example, in an embodiment, the state estimator 44 is configured to utilize the custom output measurement to estimate the unmeasured disturbances entering the process and thereby predict an operation of the chemical system based on a characterization of the chemical system by the model 42.

In an embodiment, the state estimator 44 can include an input disturbance model that is used to incorporate feedback from the location of the optimum steady-state manipulated input $u_{ss}^{opt}$ that is denoted as an infrequently observed output measurement $y_3$. In an embodiment, a correction is made for the location of the optimum state manipulated input $u_{ss}^{opt}$ or the observed output measurement $y_3$ by assigning the difference in observed and predicted values as an input disturbance d for manipulated input u in accordance with the following relationship:

$$\hat{d}_{k+1,k} = \hat{d}_{k,k-1} + (y_{3_k} - \widehat{y_3}_{k,k-1}) \tag{18}$$

where $\hat{d}_k$ is the estimate of the input disturbance based on output prediction error in $y_3$ at sampling time or control device frequency k. The above correction (equation (18)) can be made infrequently, such as only when all the criteria to observe a new steady-state optimum $y_3$ are met over the settling time $t_s$ of the control device 28, as defined above. In embodiments in which the estimate of the input disturbance stays the same, there is no correction due to a new optimum steady-state manipulated input $u_{ss}^{opt}$ or observed output measurement $y_3$, and thus:

$$\hat{d}_{k+1,k} = \hat{d}_{k,k-1} \tag{19}$$

To update a prediction of the state estimator 44, a fractional bias α of the observed error in output measurement $y_2$ is used as a constant output disturbance $\hat{p}_2$ to update the model 42. The fractional bias is calculated as:

$$\widehat{p_2}_{k+1,k} = \widehat{p_2}_{k,k-1} + \alpha(y_{2_k} - \widehat{y_2}_{k,k-1}) \tag{20}$$

In operation, an output disturbance model is used to incorporate feedback from the maximized output variable $y_1$ to obtain state estimates at control device frequency k. The estimates of the states $\hat{X}$ and the output disturbance $\widehat{p_1}$ for the output variable $y_1$ can then be obtained using the extended Kalman filter for the non-linear model 42 along with the incorporation of input disturbance estimate $\hat{d}_{k,k-1}$ as follows:

$$\hat{X}_{k+1,k} = F(\hat{X}_k, u_k, m_k, \hat{d}_{k,k-1}) + L_x(y_{1_k} - \widehat{x_1}_k - \widehat{p_1}_{k,k-1}) \tag{21}$$

$$\widehat{p_1}_{k+1,k} = \widehat{p_1}_{k,k-1} + L_{p_1}(y_{1_k} - \widehat{x_1}_k - \widehat{p_1}_{k,k-1}) \tag{22}$$

The above outlined filter ($L=[L_x, L_{p_1}]$) can then be used to provide feedback for updating the state estimates for X and $p_1$. The overall filter is time-varying due to the infrequent availability of measurement updates for the output measurement $y_3$. In an embodiment, the time-varying system can be reformulated as a time invariant raised system to obtain the filter gain.

In an embodiment, a steady-state calculator 46 is operative to determine an optimized manipulated input for operating the chemical system 10 based on the characterization of the chemical system 10 by the model and one or more steady-state output variables of the chemical system 10. In some cases, the calculator 46 can be operated as an optimizer that is configured to maintain the outputs $Y_{ss}$ at a predefined point and/or within a predefined range. In an embodiment, a non-linear steady-state target calculator 46 is configured to determine a steady-state manipulated input for operating the chemical system based on the characterization of the chemical system as calculated by the model. The steady-state calculator 46 for the outputs $Y_{ss}$, input $u_{ss}$ and states $X_{ss}$ can be evaluated using a non-linear program to minimize the deviations of the outputs from their respective setpoints $\overline{Y}$ and the deviation of the input from its current value $\overline{u}$. The setpoint $\overline{Y}$ for the output variable that is being maximized $\overline{y_1}$ is chosen at a high infeasible value to facilitate its maximization at the peak 54 where steady-state gain inversion occurs. The non-linear target tracking optimization problem can then be written as follows:

$$\min_{Y_{ss}, u_{ss}, x_{ss}} \Phi = (Y_{ss} + P - \overline{Y})^T Q_s (\overline{Y}_{ss} + P - \overline{Y}) + (u_{ss} + d - \overline{u})^T S_s (u_{ss} + d - \overline{u}) \tag{23}$$

$$P = [\widehat{p_1}_k, \widehat{p_2}_k, 0] \tag{24}$$

$$d = \hat{d}_k \tag{25}$$

in which $Q_s$ and $S_s$ are positive definite weighting matrices.

The augmented output disturbance vector is denoted as P whereas d is the input disturbance. The governing constraints for the model 42 can be expressed in the following relationships:

$$F(X_{ss}, \overline{u}_{ss}, m) = 0, Y_{ss} = X_{ss}, u_{min} \le \overline{u}_{ss} \le u_{max}, Y_{min} \le Y_{ss} \le Y_{max} \tag{26}$$

The effects of measured disturbances m and constant disturbances on the input d and outputs p are accounted for in the above formulation. During operation, in an embodiment, the input constraints are always satisfied, whereas output constraints are ranked in terms of importance and are satisfied based on assigned relative priority. Further, in an embodiment, the input disturbance estimate d is only updated when a new optimum steady-state manipulated input $u_{ss}^{opt}$ or output measurement $y_3$ is observed for steady-state conditions, whereas the output disturbance P can be estimated at every control device execution based on the bias in the output measurements $y_1$ and $y_2$. It will be appreciated, however, that the output disturbance P can be estimated at any other control device execution period or frequency without departing from the teachings provided herein.

With further reference to FIG. 3, the control device 28 also includes a regulator 48 configured to provide a signal for adjustment of one or more inputs of the chemical system 10 based on the optimized manipulated input and associated output targets. The signals are configured to actuate a control valve to control the flow of fresh olefin feed, a setpoint of the oxygen feed, a setpoint of the gas phase promoter feed, and/or a control device 28 for actuating any other variable input. In an embodiment, the control device 28 can be applied to the chemical system 10 as a supervisory control device 28, i.e., the NMPC control device 28 does not manipulate the process directly, but provides setpoints for a subordinate control device, e.g., a Linear Model Predictive control device ("LMPC") or Proportional Integral Derivative ("PID") control device. In this control structure, the NMPC control device 28 is in a supervisory mode and provides the setpoints for the lower level LMPC or PID control device. In response, the chemical system 10 is directly regulated by the PID control device according to the setpoints assigned by the NMPC control device 28. In other embodiments, a three level cascade control structure may be utilized in which the NMPC control device 28 plays a role as dynamic real-time optimization (RTO). The NMPC control device 28 calculates the optimal values of independent variables at different operating points against multiple constraints. These values pass to a secondary control device as the external targets. Then, the secondary control device determines how to move the setpoints regarding these external targets and provides the next move of setpoints to a PID control device. The PID control device directly controls the manipulated variables of the system and regulates the controlled variables of the system to setpoints assigned by secondary control device. In addition, the manipulated input can include at least one of a steady-state production rate, a steady-state chlorination effectiveness parameter (Z), or a steady-state ethylene oxide (EO) selectivity.

In an embodiment, the dynamic regulator 48 can be expressed as the following open-loop, nonlinear objective function:

$$\min_{u^k \ldots u^{k+M}} \Phi_k = \sum_{j=0}^{N} (Y_{k+j} - Y_{ss})^T Q(Y_{k+j} - Y_{ss}) + \sum_{j=0}^{M} (\Delta u_{k+j}^T S \Delta u_{k+j}), \quad (27)$$

in which Q and S are positive definite weighting matrices, N is an output horizon, and M is an input horizon. Therefore, the governing constraints for the optimization of the process are defined by various predictions of states and outputs using the output measurements up to time k, in which the constraints are defined as follows:

$$\hat{X}_{k+j+1,k} = F(\hat{X}_{k+j,k}, u_{k+j}, m_k, \hat{d}_{k+j,k}) \quad (28),$$

$$\hat{d}_{k+j+1,k} = \hat{d}_{k+j,k} \quad (29).$$

$$\hat{P}_{k+j+1,k} = \hat{P}_{k+j,k} \quad (30),$$

$$\hat{Y}_{k+j} = \hat{X}_{k+j} + \hat{P}_{k+j} \quad (31).$$

For the process described herein, the input and output constraints of the following form are considered:

$$u_{min} \leq u_{k+j} \leq u_{max}, \Delta u_{min} \leq \Delta u_{k+j} \leq \Delta u_{max}, y_{min} \leq \hat{y}_{k+j} \leq y_{max} \quad (32).$$

In an embodiment, the input constraints are always satisfied for dynamic regulation. On the other hand, the output constraints can be ranked in terms of importance and are satisfied based on priority. The vector of future open-loop control moves ($u^k \ldots u^{k+m}$) is computed from equation (27) and the first input value is injected into the plant through control of one or more variable inputs. This process can be repeated at any desired subsequent time interval with feedback using plant measurements to update the state estimates.

The control device 28 utilizes the optimum steady-state manipulated input $u_{ss}^{opt}$ as an additional infrequent output measurement that is used to update an input disturbance estimate. The location of optimum steady-state manipulated inputs (equation (4)) where controlled output is maximized $y_{1_{ss}}^{opt}$ depends on measured disturbances m and can be used to update the input disturbance estimate. Accurate identification of the input disturbance is problematic with using $y_1$ directly due to associated input multiplicity. Thus, robust identification of input multiplicity can be important for a control device 28 that has the goal of staying at, or proximate to, the peak 54 of a process having a steady-state gain inversion with noisy industrial data as measurements. It is also conceivable that the chemical system 10, and/or the control device 28, described herein can also be used for processes that exhibit steady-state gain inversion at a minimum instead of a maximum with the control objective of minimizing at the trough, e.g. operating costs.

In an embodiment, the control device 28 described herein is used in an industrial ethylene epoxidation reactor 12 to maximize the selectivity for ethylene oxide production in the reactor. The closed-loop control device 28 has resulted in significant commercial value by achieving an average gain of 0.5-1 percent in EO selectivity compared to optimizing selectivity manually.

By way of example, and not limitation, some embodiments of the present disclosure are described in detail in the following example.

EXAMPLE

A control device for a chemical system implementing a process with steady-state gain inversion is applied to maximize the selectivity of reaction to ethylene oxide (EO). Ethylene oxide is produced by using silver based catalysts for selective oxidation of ethylene to ethylene oxide thereby minimizing secondary reactions that decrease ethylene oxide (EO) selectivity. For conventional catalysts, EO selectivity does not reach values above 85.7 percent, which had long been considered as the theoretical maximum selectivity for the following overall reaction:

$$7C_2H_4 + 6O_2 \rightarrow 6C_2H_4O + 2CO_2 + 2H_2O \quad (33).$$

Some industrial ethylene epoxidation reactors use co-fed chlorination promoters that are adsorbed on the catalyst to modify, by promoting or moderating, certain reaction pathways and in this way increasing selective oxidation to ethylene oxide. High efficiency industrial catalysts tend to exhibit relatively steep parabolic curves for EO selectivity as a function of effective gas-phase chloride concentration that can be measured as a dimensionless chlorination effectiveness parameter Z. An empirical steady-state model relates the EO selectivity $EO_{sel}$ to a chlorination effectiveness parameter Z that is dependent on partial pressures. The location of the peak or optimum EO selectivity is also a strong function of reaction temperature that is used to control EO production rate.

The objective of the feedback control device is to maximize EO selectivity $EO_{sel}$ by manipulating the chlorination effectiveness parameter Z in the presence of disturbances due to EO production rate $EO_{prod}$ and inlet oxygen concentration $iO_2$. The process operational limits for, as an example, ethyl chloride flow $EC_{flow}$ are ranked as more important than maximizing EO selectivity $EO_{sel}$ so that the process operational limits can limit maximization of EO selectivity $EO_{sel}$ at extreme conditions. The location of a peak where EO selectivity $EO_{sel}$ with respect to Z reaches a maximum and the steady-state gain changes sign is dependent on measured disturbances and unmeasured disturbances. Unmeasured disturbances that include catalyst over/ under performance compared to prediction for its age also affect the location of the peak. Steady-state variation of EO selectivity $EO_{sel}$ with respect to Z at different production rates that acts as a measured disturbance is shown in FIG. 4. Prior to the implementation of the control device provided herein, the steady-state non-linear process model was used to calculate open-loop targets for Z and corrections were done manually based on observed EO selectivity $EO_{sel}$.

A validated empirical steady-state model is used along with first order dynamics to capture the information in the process output measurements. First order dynamics with varying steady-state gains (multiplier of 1-10) and time constants (multiplier of 1-2) are used to define the effect of inputs u, m on outputs y. The steady-state nonlinear model (equations (6), (7) and (8)) has the following variables:

$$u=[Z] \quad (34),$$

$$m=[EO_{prod}, iO_2] \quad (35),$$

$$Y=[EO_{sel}, EC_{flow}, Z_{ss}^{opt}] \quad (36),$$

where u is the manipulated inputs, m is the measured disturbances, and Y is the controlled outputs. $Z_{ss}^{opt}$ is the optimum steady-state value of manipulated input Z that maximizes $EO_{sel}$ at steady conditions and is used as a custom measurement $y_3$. The steady-state non-linear model for the outputs Y are calculated as:

$$EO_{sel}(\text{percent}) \quad (37)$$
$$= 93.159 - 0.0274 * (EO_{prod}/1000) + 0.16 * iO_2 - 0.286$$
$$* [0.0115 * (EO_{prod}/1000) - 0.316 * iO_2 + 5.143] - 0.399 * [Z$$
$$- (0.0115 * (EO_{prod}/1000) - 0.316 * iO_2 + 5.143] - 1.19$$
$$* [Z - (0.0115 * (EO_{prod}/1000) - 0.316 * iO_2 + 5.143]^2,$$

$$EC_{flow}(\text{lb/hr}) = 0.868 - 1.374 * Z, \quad (38)$$

$$Z_{ss}^{opt} = 4.975 + 0.0115 * (EO_{prod}/1000) - 0.316 * iO_2, \quad (39)$$

where the measured disturbance m for $EO_{prod}$ is measured in lb/hr and $iO_2$ is expressed as a percent. $EO_{sel}$ has first order dynamics with a dead-time of 30 minutes and time constant of 5 hours at a normal EO production rate $EO_{prod}$. In addition, $EO_{flow}$ has first order dynamics with no dead-time and a time constant of 2 hours at the normal EO production rate $EO_{prod}$. The time constants for $EO_{sel}$ and $EO_{flow}$ vary with EO production rates $EO_{prod}$. $Z_{ss}^{opt}$ is the steady-state value of optimum Z and does not have time-varying dynamics.

The discretized state space model is calculated at a frequency provided in equations (16) and (17) along with the validated empirical steady-state model and is used by the control device 28 to maximize EO selectivity $EO_{sel}$ or the maximized output variable $y_1$. Hierarchical control is used as the primary control device, having NMPC implemented therein, that maximizes EO selectivity by manipulating chloriding effectiveness parameter Z that is regulated by a faster secondary PID control device.

The primary control device, utilizing NMPC, is used to maximize EO selectivity $EO_{sel}$ by manipulating chloriding effectiveness parameter Z every 15 minutes. Slower execution time for the primary control device is sufficient because the models for EO selectivity have a long settling time, and is also needed because of the higher computational needs of the associated dynamic optimization problem. The NMPC models for EO selectivity $EO_{sel}$ described herein are non-linear and have a long settling time of 6-12 hours depending on EO production rates. The NMPC models are tuned appropriately to get the desired control action. The control objectives for NMPC models are ranked so that the operating limits for ethyl chloride flow $EC_{flow}$ or $y_2$ are most important, followed by maximizing $EO_{sel}$ or the maximized output variable $y_1$, as outlined in Table 1.

TABLE 1

| Control Device Objective | Relative Ranking (Priority) |
| --- | --- |
| Limits for Ethyl Chloride Flow | 1 |
| Limits for EO Selectivity | 2 |
| EO Selectivity Target | 3 |
| Limits for optimum Z | 4 |

These rankings are enforced both during steady-state target optimization (equation (23)) and dynamic regulation (equation (27)). The limits on the operational limit $y_2$ or output measurement $y_3$ do not become active for normal plant operations thereby allowing for maximization of EO selectivity $EO_{sel}$ or the maximized output variable $y_1$. Maximization of EO selectivity $EO_{sel}$ is achieved by giving it a very high infeasible target. The operating limits for the manipulated input for the chloriding effectiveness parameter Z and the outputs y are shown in Table 2.

TABLE 2

| Variable | Lower Limit | Upper Limit |
| --- | --- | --- |
| Z (u) | 3 | 8.0 |
| EO Selectivity ($y_1$) | 75 Percent | 95 Percent |
| Ethyl Chloride Flow ($y_2$) | 0.5 lb/hr | 12 lb/hr |
| Optimum Z ($y_3$) | 3 | 8.0 |

The limits on the movement of the manipulated input for the chloriding effectiveness parameter Z for dynamic regulation (equation (32)) are sufficiently small to prevent it from moving faster than underlying process and process control can respond.

The input horizon M is set to three hours and output horizon N is set to 12 hours (equation (27)) for the control device. The quadratic penalty on the deviation of the outputs Q, $Q_s$ from their desired values $\bar{y}$ is set to its nominal value to get the same relative value for each output (equations (23) and (27)) such that:

$$Q_s = Q = \frac{2}{\bar{y}^2}. \quad (40)$$

The quadratic penalty on the rate of change of the manipulated input for the chloriding effectiveness parameter Z (S) is set for steady-state target calculation, which may be an optimization function, and dynamic regulation (equations (23) and (27)) after taking into account its lower and upper operating limits, which are presented in Table 2, such that $$S=0.025 \quad (40).$$

The moves for the chloriding effectiveness parameter Z are implemented by passing them as targets to the secondary LMPC or PID control device that controls the chloriding effectiveness parameter Z by manipulating ethyl chloride flow $EC_{flow}$ every second to reject faster disturbances.

Appropriate data screening and filtering are implemented on noisy EO selectivity measurements y. Erroneous analyzer data due to bad measurement analysis can provide inappropriate values of calculated EO selectivity for the control device. Appropriate feedback is ensured by checking the analyzer data against validity limits before using it for EO selectivity $EO_{sel}$ calculations.

Figure 5:
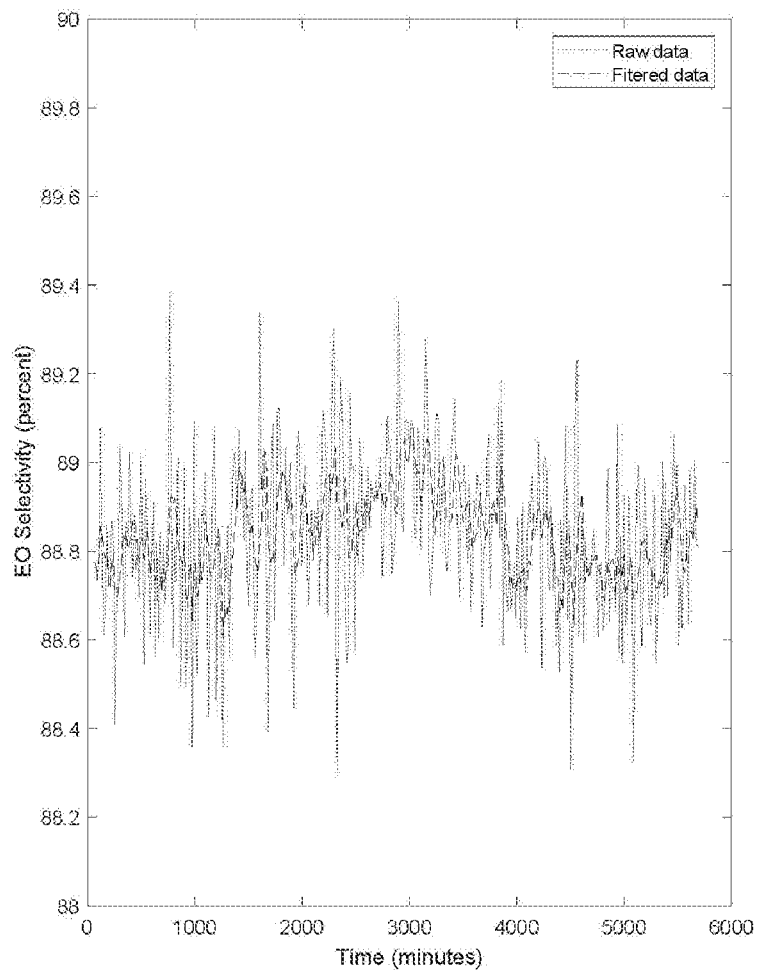
FIG. 5 is a graph depicting EO selectivity based upon baseline data, in accordance with an embodiment of the present disclosure.
Figure 6:
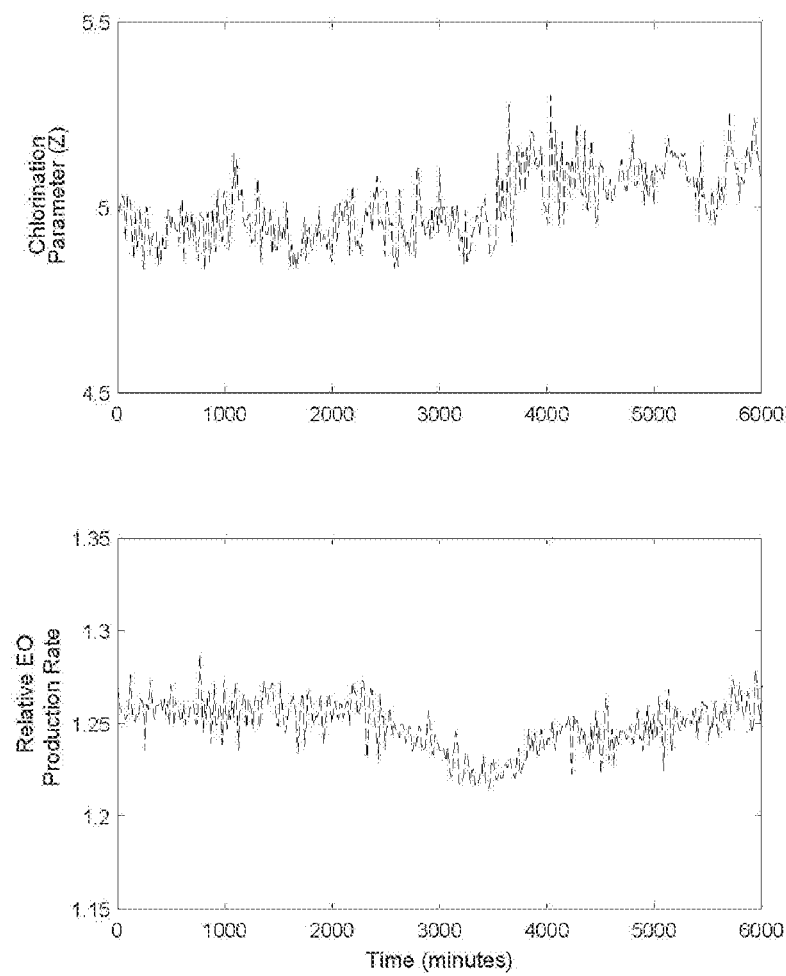
FIG. 6 is a pair of graphs depicting a chloriding effectiveness parameter Z and an EO production rate over time based upon baseline data, in accordance with an embodiment of the present disclosure.

In operation, baseline plant data showing management of EO selectivity with operating discipline prior to the implementation of a NMPC control device is illustrated in FIGS. 5 and 6. As illustrated, selectivity did not increase consistently even though the production rate decreased from time=2400 minutes to time=3500 minutes because the chloriding effectiveness parameter Z was not adjusted appropriately. In addition, selectivity dropped around time=3800 minutes due to a production rate increase at time=3600 minutes. The higher chloriding effectiveness parameter Z due to open-loop implementation helped to attain a higher selectivity at time=5500 minutes. However, there are losses in EO selectivity $EO_{sel}$ due to delays and limitations associated with the open-loop implementation of targets for the chloriding effectiveness parameter Z.

Conversely, EO selectivity $EO_{sel}$ has been maximized more effectively using the NMPC control device described herein than the old control scheme that used the steady-state non-linear process model to calculate open-loop targets for the chloriding effectiveness parameter Z, resulting in an average gain of 0.5-1 percent in selectivity for the industrial process. The NMPC application maximizes EO selectivity $EO_{sel}$ based on three scenarios, which include:
1. EO Selectivity control at high EO production rate;
2. EO Selectivity control with increasing EO production rate; and
3. EO Selectivity control for a big unmeasured disturbance.

The limits for Ethyl chloride flow $EC_{flow}$ are wide and do not become active constraints in the above three scenarios so the chloriding effectiveness parameter Z is available for maximization of EO selectivity $EO_{sel}$.

Figure 7:
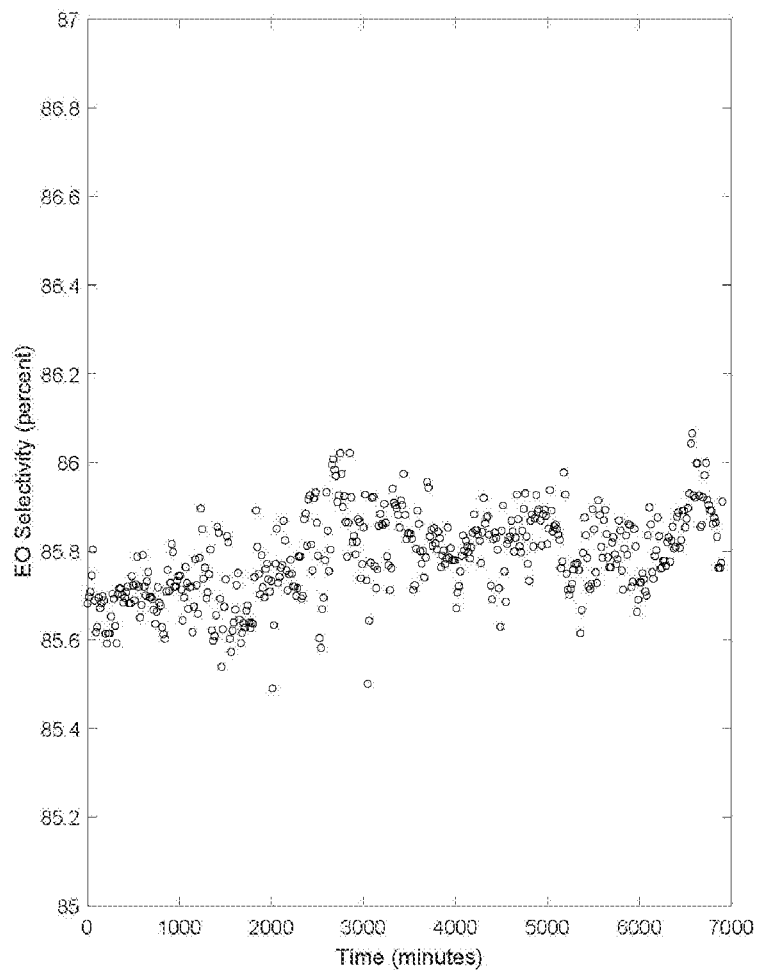
FIG. 7 is a graph depicting EO selectivity based upon usage of the NMPC device at a high production rate, in accordance with an embodiment of the present disclosure.
Figure 8:
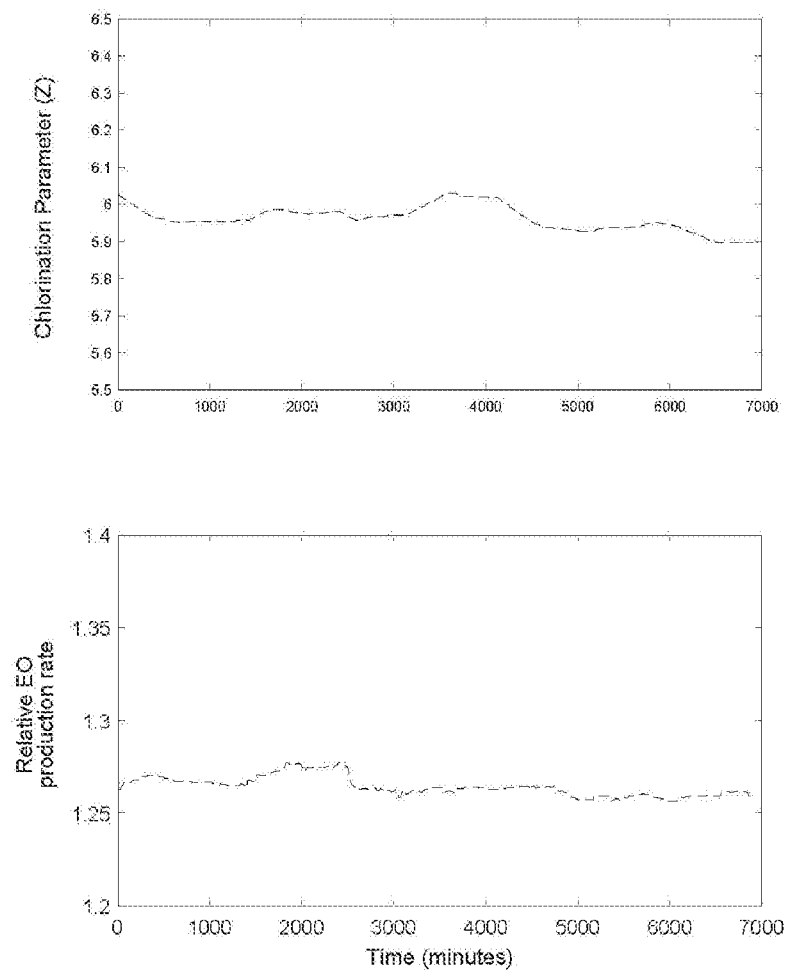
FIG. 8 is a graph depicting is a pair of graphs depicting a chloriding effectiveness parameter Z and an EO production rate over time based upon usage of the NMPC device at a high production rate, in accordance with an embodiment of the present disclosure.

FIG. 7 shows how EO selectivity $EO_{sel}$ is maximized and perturbed around the optimum by manipulating the chloriding effectiveness parameter Z at high EO production rates, which are illustrated in FIG. 8. Inlet oxygen concentration stays relatively constant during that time period. The final chloriding effectiveness parameter Z value is smaller as the optimum value is lower for maximization of EO selectivity $EO_{sel}$. Perturbation around the optimum due to the input disturbance model ensures effective maximization of EO selectivity $EO_{sel}$.

Figure 9:
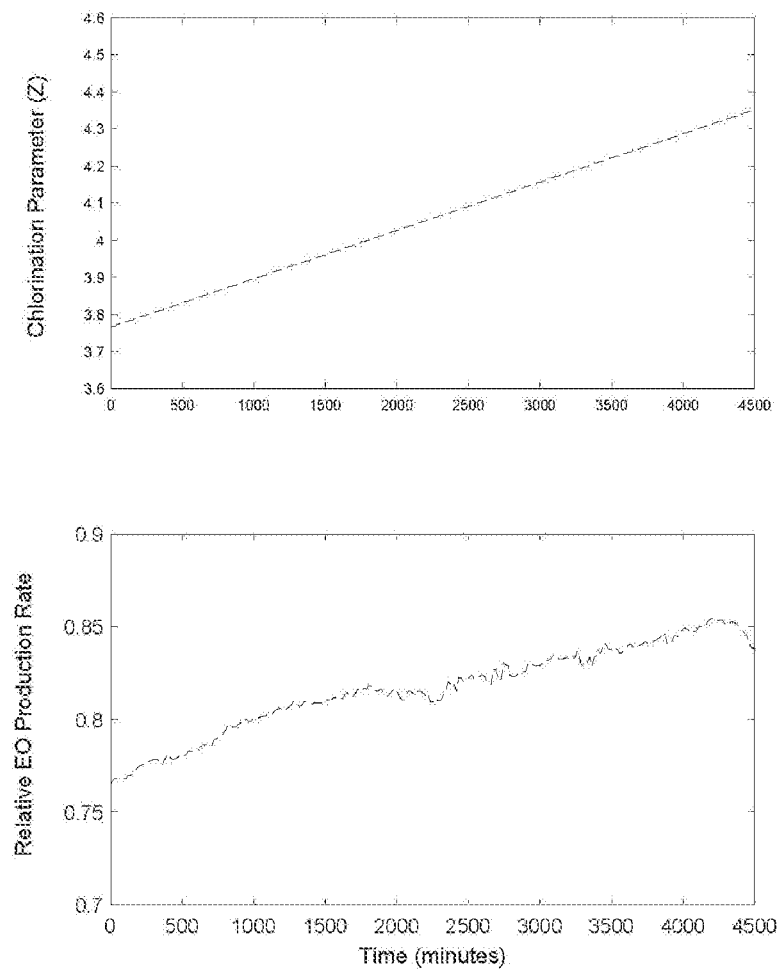
FIG. 9 is a graph depicting is a pair of graphs depicting a chloriding effectiveness parameter Z and an EO production rate over time based upon usage of the NMPC device with an increasing production rate, in accordance with an embodiment of the present disclosure.
Figure 10:
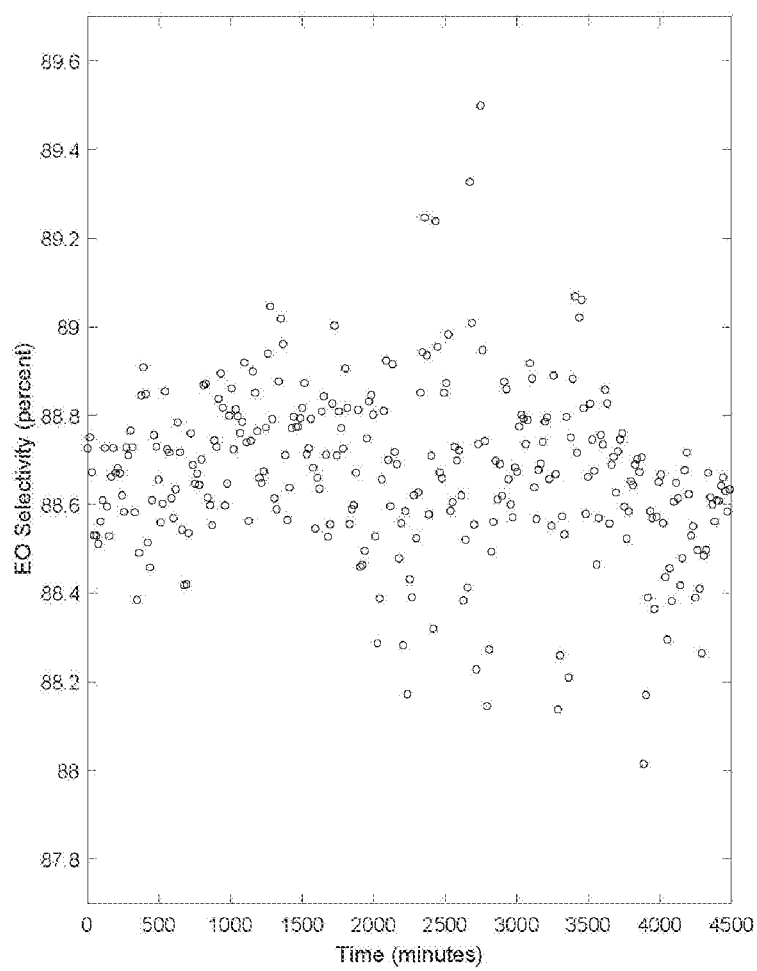
FIG. 10 is a graph depicting EO selectivity based upon usage of the NMPC device with an increasing production rate, in accordance with an embodiment of the present disclosure.

The control device was also in use when the ethyl epoxidation reactor was ramping rates from a low production rate to a higher production rate, which is illustrated in FIG. 9. The manipulated input for the chloriding effectiveness parameter Z increases with EO production rate over three days, as illustrated in FIG. 10, because its optimum value to keep the EO selectivity $EO_{sel}$ maximized is increasing. In addition, inlet oxygen concentration stays relatively constant during that time period.

Figure 11:
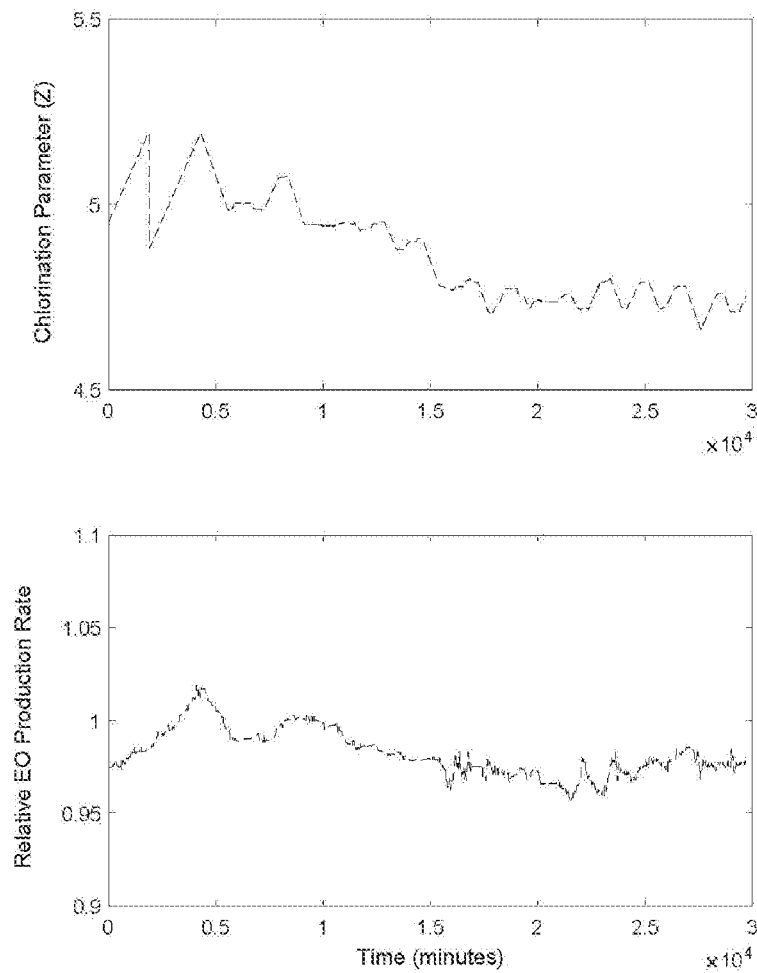
FIG. 11 is a graph depicting is a pair of graphs depicting a chloriding effectiveness parameter Z and an EO production rate over time based upon usage of the NMPC device with an unmeasured disturbance, in accordance with an embodiment of the present disclosure.
Figure 12:
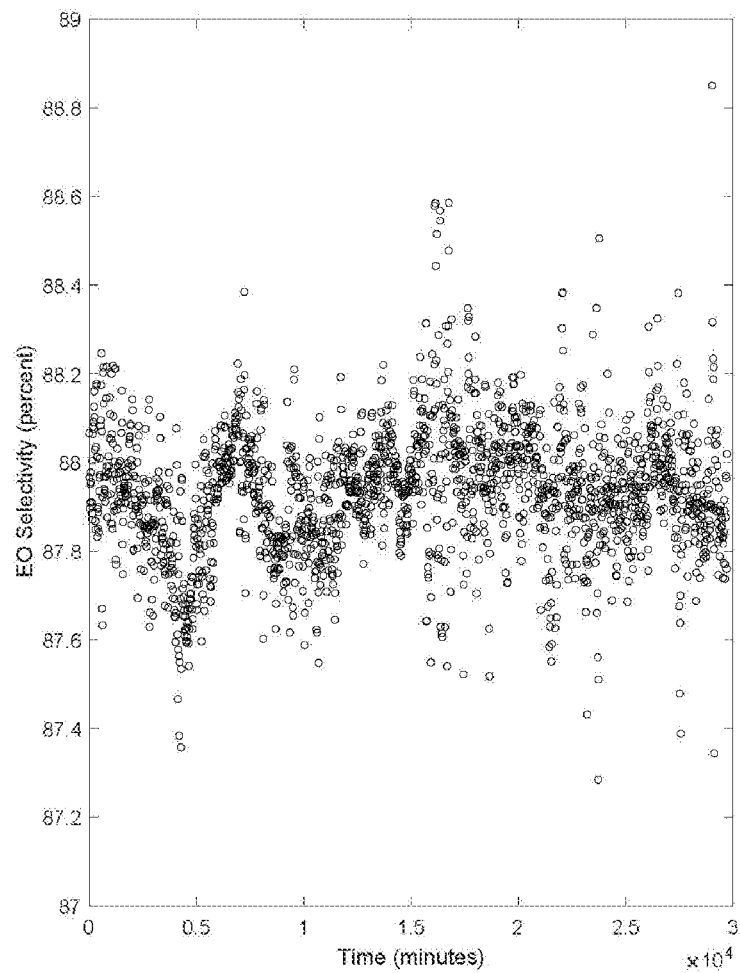
FIG. 12 is a graph depicting EO selectivity based upon usage of the NMPC device with an unmeasured disturbance, in accordance with an embodiment of the present disclosure.

In the example illustrated in FIGS. 11 and 12, one of the measurement analyzers is swapped for a back-up analyzer at time=200 minutes leading to a drop in measured chloriding effectiveness parameter Z, even though the real chloriding effectiveness parameter Z has not changed. Thus, the control device 28 responds by increasing $EC_{flow}$ to increase measured chloriding effectiveness parameter Z, which leads to higher chlorination and the subsequent drop in EO selectivity $EO_{sel}$. When this is detected by the control device 28, the chloriding effectiveness parameter Z starts decreasing at time=400 minutes to compensate for over-chlorination, leading to higher EO selectivity $EO_{sel}$. The chloriding effectiveness parameter Z stops decreasing around time=1750 minutes settling and oscillating around the optimum to keep the EO selectivity $EO_{sel}$ maximized. Appropriate data screening criteria have been added to detect analyzer swaps and re-calibration is contemplated to prevent associated unmeasured disturbances for various implementations of the control device.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A chemical system for an operation exhibiting steady-state gain inversion, the system comprising:
   a reactor configured to receive a feed stream and produce an outlet stream to form a process; and
   a control device configured to control the process, wherein the control device receives inputs indicative of an operational parameter and output variables and, in response to the inputs and output variables, provides a steady-state manipulated input configured to control or optimize the process, the control device including:
      an input disturbance model based on using the steady-state manipulated input as a custom output measurement to determine unmeasured disturbances,
      a state estimator configured to utilize the custom output measurement to estimate the unmeasured disturbances entering the process and thereby predict a change in the process based on a characterization of the process by the model,
      a non-linear steady-state target calculator configured to determine the steady-state manipulated input for the process based on the characterization of the process as calculated by the model, and
      a regulator configured to provide a signal for adjustment of one or more inputs based on the steady-state manipulated input and associated output variables, wherein the regulator determines a change in the manipulated input to optimize the output variable based on an observation of a gain inversion over a settling time of the control device if the manipulated input to maximize the variable output is within an operational threshold, one or more measured disturbances are steady as based on statistical criteria, the manipulated input is steady or moving towards an optimum steady-state manipulated input, and a new optimum optimized manipulated input is observed after a settling time of the control device.

2. The chemical system of claim 1, wherein the calculator is configured to determine an optimum range for the steady-state manipulated input.

3. The chemical system of claim 1, wherein the model includes at least one of a fundamental first principles model, an empirical model, an adaptive model, a fuzzy model or a neural network model with dynamics.

4. The chemical system of claim 1, wherein the control device maximizes the output variable that exhibits steady-state gain inversion with respect to the manipulated input (u) through the relationship:

$$y_{1_{ss}} = l(u_{ss}, m)$$

wherein $u_{ss}$ the steady-state manipulated input, m is the measured disturbances, and $y_{1_{ss}}$ is an output variable that exhibits steady-state gain inversion.

5. The chemical system of claim 1, wherein the control device comprises a nonlinear model predictive control (NMPC) device as a primary controller to address real-time computational needs and a linear model predictive controller (LMPC) or a proportional-integral-derivative (PID) controller for executing one or more moves of the NMPC.

6. The chemical system of claim 1, wherein the control device is configured to estimate the unmeasured disturbances that shift a position of the optimum peak where steady-state gain inversion occurs, the unmeasured disturbances including catalytic aging and associated over/under performance of the reactor.

7. The chemical system of claim 1, wherein the manipulated input includes at least one of a steady-state production rate, a steady-state chloriding effectiveness parameter, or a steady-state ethylene oxide (EO) selectivity.

8. The chemical system of claim 1, wherein the output variable is intermittently maximized by using an output disturbance model along with a high infeasible target for the calculator and the regulator.

9. The chemical system of claim 1, wherein the manipulated input includes at least one of chlorination effectiveness parameter (Z) or ethylene oxide (EO) production rate to control ethylene oxide (EO) selectivity.

10. The chemical system of claim 1, wherein the control device is configured to optimize a selectivity of effluent ethylene oxide (EO) in the reactor.

11. A method for controlling a chemical system through a control device, the method comprising:

receiving inputs indicative of an operational parameter of a process and a steady-state output variable;

implementing an input disturbance model based on using an optimum manipulated steady-state input as a custom output measurement to determine the optimized manipulated input in a presence of both measured and unmeasured disturbances;

estimating a state of the process to predict the process based on a characterization of the process by the model;

determining a targeted manipulated input for the process based on the characterization of the process by the modelling and the estimating of the one or more steady-state output variables of the chemical system; and regulating the process based on the targeted manipulated input, wherein regulating the process includes determining a change in the manipulated input to optimize the output variable based on an observation of a gain inversion over a settling time of the control device if the manipulated input to maximize the variable output is within an operational threshold, one or more measured disturbances are steady based on statistical criteria, the manipulated input is steady or moving towards an optimum steady-state manipulated input, and a new optimum optimized manipulated input is observed after a settling time of the control device.

12. The method of claim 11, wherein the regulating of the chemical system based on the optimized manipulated input includes manipulating at least one of a chlorination effectiveness parameter (Z) or an ethylene oxide (EO) production rate to control an ethylene oxide (EO) selectivity.

13. The method of claim 11, wherein the regulating the chemical system based on the optimized manipulated input includes maximizing a steady-state gain inversion proximate to a value in which sign change indicating a change from a rise in selectivity to a decrease in selectivity occurs.

14. The method of claim 11, wherein the regulating of the chemical system is configured to optimize a selectivity of effluent ethylene oxide (EO) in an epoxidation reactor.

* * * * *